US007770476B2

(12) United States Patent
Davis et al.

(10) Patent No.: US 7,770,476 B2
(45) Date of Patent: Aug. 10, 2010

(54) CAPTURING AIR SAMPLES FOR FORENSIC INVESTIGATION

(75) Inventors: Brian Jeffrey Davis, Raleigh, NC (US); Timothy Clay Doyle, Cary, NC (US); Todd Donald McCormack, Durham, NC (US)

(73) Assignee: International Business Machines Corporation, Armonk, NY (US)

( * ) Notice: Subject to any disclaimer, the term of this patent is extended or adjusted under 35 U.S.C. 154(b) by 263 days.

(21) Appl. No.: 11/944,701

(22) Filed: Nov. 26, 2007

(65) Prior Publication Data

US 2009/0133513 A1 May 28, 2009

(51) Int. Cl.
*G01N 1/12* (2006.01)

(52) U.S. Cl. .................................................. 73/864.51

(58) Field of Classification Search .................. 73/864, 73/864.51, 863.01

See application file for complete search history.

(56) References Cited

U.S. PATENT DOCUMENTS 4,281,545 A 8/1981 Linder
4,338,826 A 7/1982 Jacoby et al. ............ 73/864.62
4,818,489 A 4/1989 Gonner et al. ................ 422/84
4,909,089 A 3/1990 Achter et al. ............ 73/863.11
5,211,286 A * 5/1993 Turner ........................ 206/223
5,333,511 A 8/1994 Boyum et al. ............ 73/864.34
5,410,918 A 5/1995 Zimmerman ................. 73/864
6,729,196 B2 5/2004 Moler et al. ............. 73/863.22
6,952,945 B2 10/2005 O'Brien ..................... 73/23.35
7,100,424 B2 9/2006 Wilson ...................... 73/31.05
7,159,475 B2 1/2007 Casillas et al. ........... 73/864.34
7,191,670 B2 3/2007 Aicher ........................ 73/863
2004/0063198 A1 * 4/2004 Tilles et al. .............. 435/287.2
2006/0073471 A1 4/2006 Bango et al. ................... 435/4

* cited by examiner

*Primary Examiner*—Hezron Williams
*Assistant Examiner*—Tamiko D Bellamy
(74) *Attorney, Agent, or Firm*—Cynthia G. Seal; Jeffrey L. Streets

(57) ABSTRACT

In one embodiment, air is automatically sampled within a zone of interest in response to an event caused by a mammal. The release of material from the mammal may be induced by directing an increased velocity airflow at the mammal or by introducing a sneezing agent into the zone of interest and capturing the air sample after the mammal has sneezed. Materials contained within the sampled air may include organic material such as skin, hair, saliva, or mucus, and gases such as CO2 and methane. The materials may be forensically analyzed to confirm the presence or to determine the identity of the mammal. The organic materials may contain DNA, in which case the forensic analysis may include a DNA analysis to determine the identity of the mammal.

18 Claims, 3 Drawing Sheets

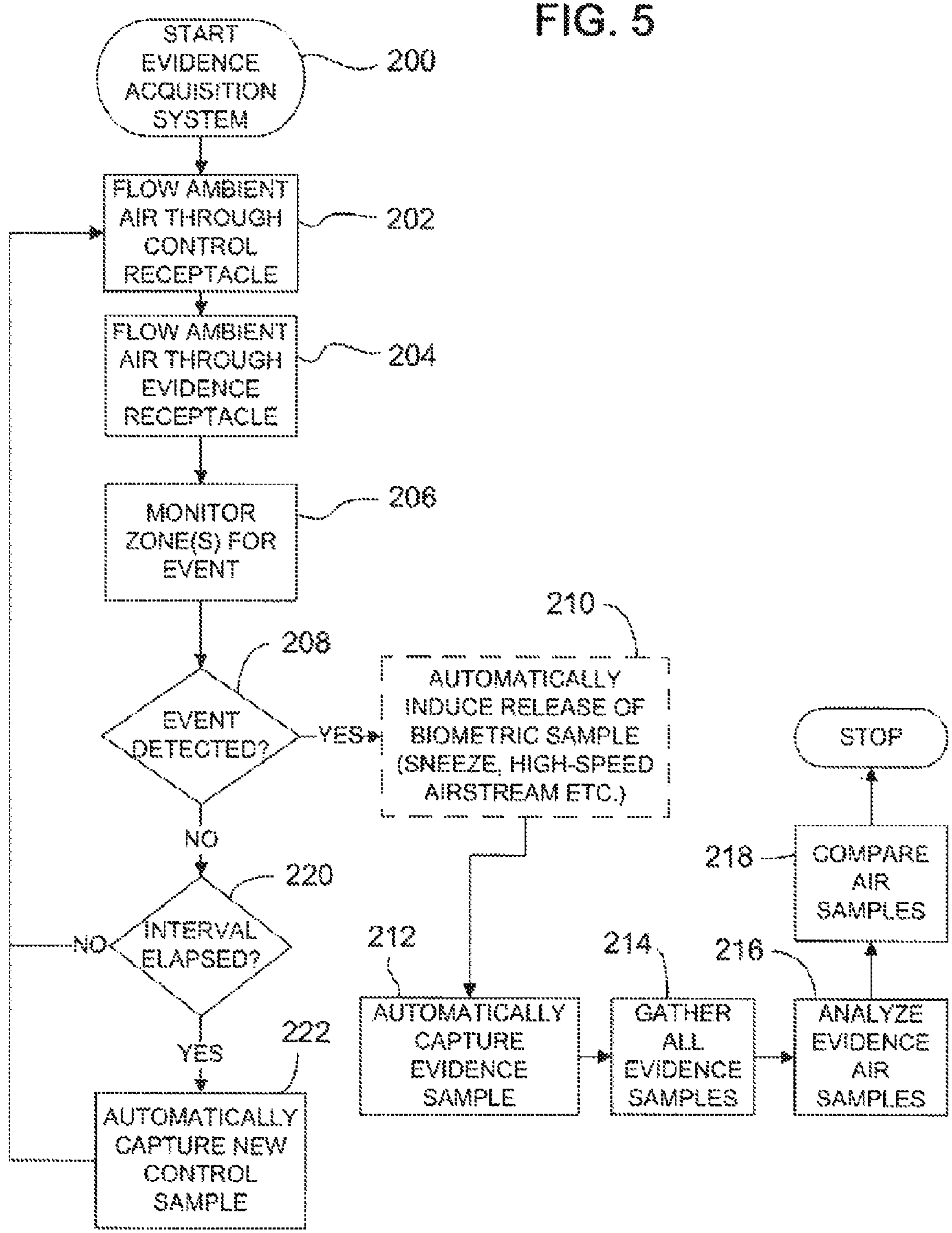
FIG. 5
START EVIDENCE ACQUISITION SYSTEM
200
FLOW AMBIENT AIR THROUGH CONTROL RECEPTACLE
202
FLOW AMBIENT AIR THROUGH EVIDENCE RECEPTACLE
204
MONITOR ZONE(S) FOR EVENT
206
EVENT DETECTED?
208
YES
NO
210
AUTOMATICALLY INDUCE RELEASE OF BIOMETRIC SAMPLE (SNEEZE, HIGH-SPEED AIRSTREAM ETC.)
INTERVAL ELAPSED?
220
NO
YES
222
AUTOMATICALLY CAPTURE NEW CONTROL SAMPLE
212
AUTOMATICALLY CAPTURE EVIDENCE SAMPLE
214
GATHER ALL EVIDENCE SAMPLES
216
ANALYZE EVIDENCE AIR SAMPLES
218
COMPARE AIR SAMPLES
STOP

CAPTURING AIR SAMPLES FOR FORENSIC INVESTIGATION

BACKGROUND OF THE INVENTION

1. Field of the Invention

The present invention relates to forensic investigations at the scene of an event, such as a crime, tort, or accident. In particular, the invention relates to capturing air samples and forensically analyzing the components of the air samples.

2. Description of the Related Art

Forensic science (often referred to as forensics) is the application of a broad spectrum of sciences to answer questions of interest to the legal system. Forensics typically includes collecting and examining evidence at a scene where an event has occurred, such as a crime or accident. In the context of a criminal investigation or a civil action, the results of forensic analysis may be used to prove or disprove facts in support of legal theories. For example, the general public is aware of such techniques as "DNA analysis" of organic evidence such as skin and bodily fluid samples used to help pinpoint the perpetrator of a crime. The term "forensics" is used more broadly herein to also include the gathering of evidence for analysis of an accident scene or other event (not necessarily the occurrence of a crime or tort), where physical and organic evidence may be used to scientifically evaluate the cause of the event, as well as the identity of people who were present during the event.

The use of forensics often presupposes an unfortunate reality—that the perpetrator of a crime or tort is usually gone from the scene by the time authorities can arrive to ascertain their identity. The identity of a suspect must then be investigated forensically. Law enforcement officials have a variety of investigative tools at their disposal that can be used to gather any remnants of evidence, organic or otherwise, left behind by the perpetrator. However, it is often a matter of luck whether and to what degree such traces are left behind. If forensic evidence at a scene is limited, non-existent, or contaminated, the cause and perpetrator of an event may be undetectable.

New or improved investigative techniques are, therefore, sought in view of the limitations of conventional forensic and evidence-gathering techniques, and in recognition of the fact that forensic evidence is often limited or non-existent. In particular, investigative techniques are sought that would increase the likelihood of obtaining a useful evidentiary sample from the scene of an event and increase the reliability and usefulness of forensic analysis.

SUMMARY OF THE INVENTION

In a first embodiment, an evidence air sample is automatically captured in a sealed container. The evidence air sample contains material from a mammal after the entrance of the mammal into a zone of interest. The material in the evidence air sample is analyzed to determine the entrance of the mammal within the zone of interest or to determine the identity of the mammal.

In a second embodiment, a control air sample is captured from a zone of interest prior to an entrance of a mammal into the zone of interest. An evidence air sample containing material from the mammal after the entrance of the mammal into the zone of interest is automatically captured in a sealed container. The material in the evidence air sample is analyzed to identify characteristics of the mammal.

A third embodiment is a system that includes an airflow system configured for moving air from the zone of interest into an air-sampling container and selectively closing airflow to the air-sampling container. A controller is configured for selectively closing the airflow to the container in response to an event caused by a mammal that enters the zone of interest, to capture an air sample from the zone of interest within the air-sampling container.

Other embodiments, aspects, and advantages of the invention will be apparent from the following description and the appended claims.

BRIEF DESCRIPTION OF THE DRAWINGS

FIG. 1 is a schematic diagram illustrating the collection of an air sample containing material from a person.

FIG. 2 is a schematic diagram of an air sampling system that may be used to collect air samples containing material from a mammal.

FIG. 5 is a flowchart outlining an embodiment of an air sampling method according to the invention.

DETAILED DESCRIPTION OF PREFERRED EMBODIMENTS

Figure 3:
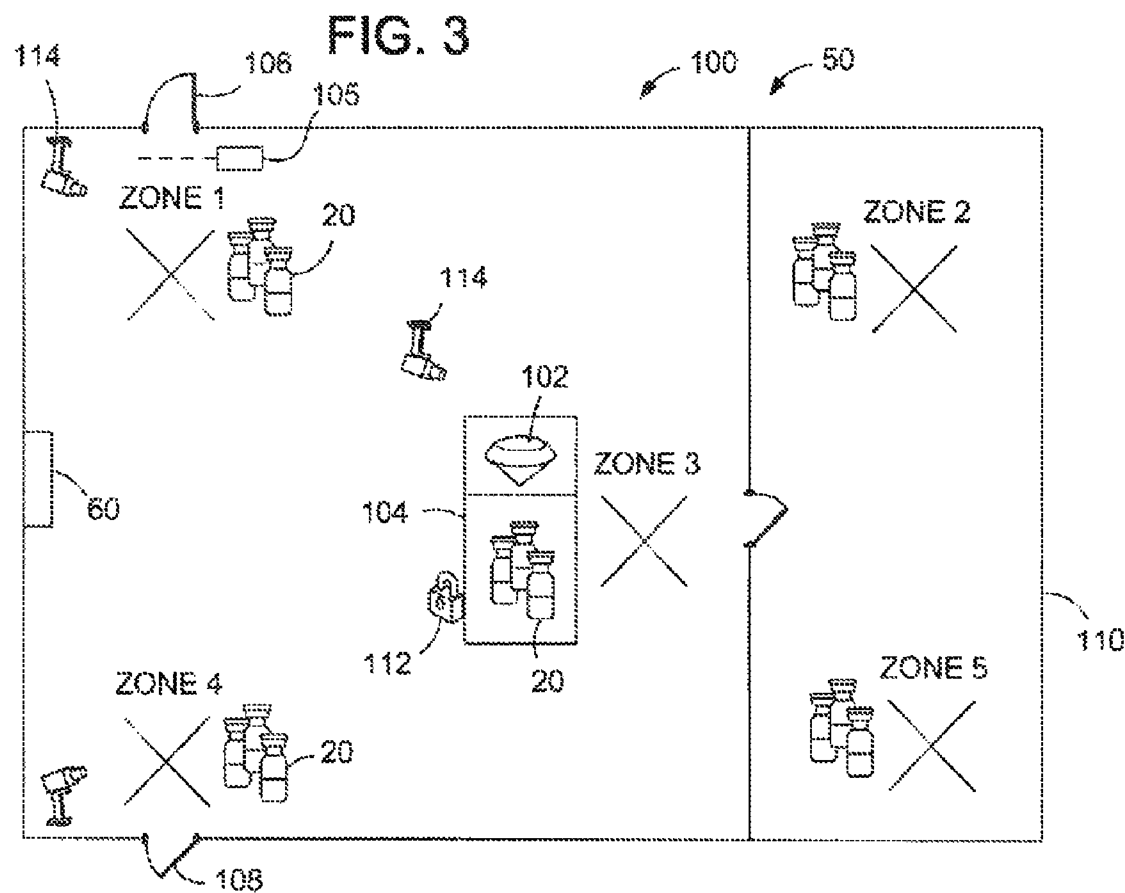
FIG. 3 is schematic diagram of an exemplary site equipped with the air sampling system.

The present invention provides improved systems and methods for use in forensic analysis of the scene of an event to be investigated, such as a crime scene or accident scene. The invention includes methods for automatically collecting air samples in response to the triggering of an event that may involve the presence of one or more humans. One or more air samples (the "control air samples") may be taken periodically from within a zone of interest, prior to the occurrence of the event to be investigated. Upon the occurrence of the event, at least one other air sample (the "evidence air sample") may be taken in the zone of interest. If a human was present in the zone of interest, then the evidence air sample may contain material from or present on the person, such as skin, hair, saliva, mucus, carbon dioxide ($CO_2$), or methane. Some of these materials may be organic, and some may even contain deoxyribonucleic acid (DNA), which is particularly useful in identifying the person using any of a variety of DNA tests known in the art. The expulsion of organic materials like skin, hair, saliva, or mucus from the human may be induced to increase the likelihood that a sample containing DNA will be obtained. The evidence air samples may be compared to the control air samples to identify characteristics and/or verify the presence of the perpetrator. The evidence sample may also be analyzed, such as by performing a DNA analysis on exfoliated skin particles or hair captured in the evidence air sample, for identifying the perpetrator. Because humans are often the cause of an event to be forensically investigated, the embodiments discussed below will be largely discussed in the context of events caused by humans. However, the invention may also be used in the forensic analysis of material from mammals other than humans, such as in the case of a wild animal attack.

Figures 1, 2:
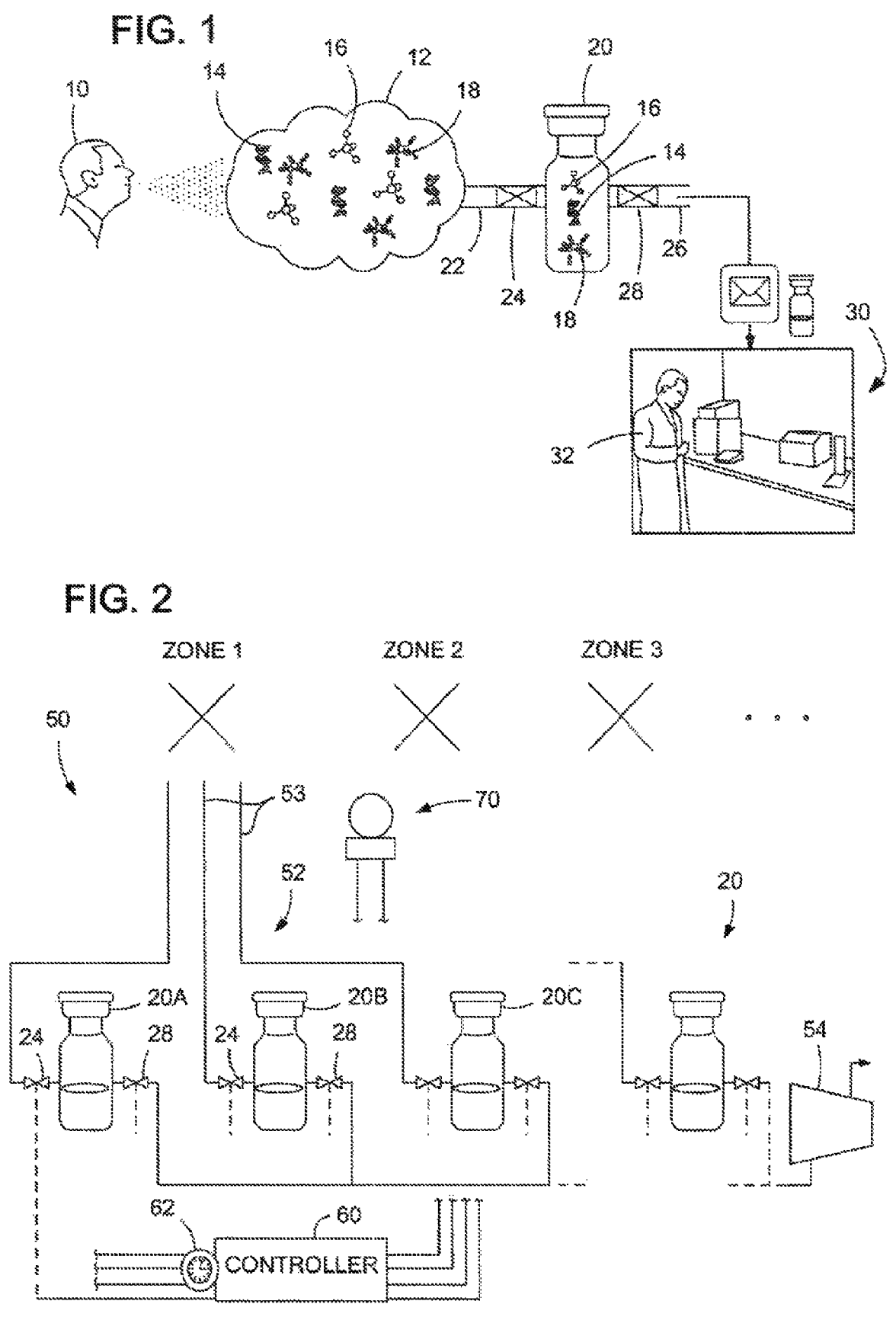

FIG. 1 is a schematic diagram illustrating the collection of an air sample containing both organic and inorganic material from a person 10. The person 10 is sneezing, which is one example of how organic material such as saliva, mucus, skin and other tissues, hair, and inorganic materials like $CO_2$ and other exhaled gases may be emitted into the air. Additional organic and inorganic materials may be expelled from the person 10 without sneezing, such as through breathing, talking, and exfoliating. The air 12 in the immediate vicinity of the person 10 is graphically depicted as containing (by way of example) traces of DNA 14, methane 16, and $CO_2$ molecules 18, and may contain other identifying materials too. An air-sampling container, which in this case is a sealed specimen container 20, is used for capturing an air sample and includes an air inlet port 22, inlet valve 24, air outlet port 26, and outlet valve 28. Airflow may be established through the container 20, such as using a vacuum or pressurized air. When a triggering event is detected, an evidence air sample may be captured in the container 20 by passing a portion of the air 12 into the container 20 and closing the valves 24, 28. The contents of the container 20 may then be sent to a laboratory 30 for further testing. For example, a lab technician 32 may analyze the DNA 14 in the sample to determine the identity of the person 10, or analyze the concentrations of methane 16, $CO_2$ 18, and other gases to determine if they are consistent with human presence. Even simply determining or confirming whether or not humans or animals were present at a scene may help investigators determine whether or not the cause of an event is attributable to the humans or animals. An electronic odor detector may also be used in the detection and analysis of the collected materials either contemporaneously with the event or afterwards in the laboratory 30.

FIG. 2 is a schematic diagram of an air sampling system 50 according to one embodiment of the invention. The air sampling system 50 may be used to collect air samples containing material from a site that has the potential of becoming the scene of an event. For example, the site may be a bank, which has the potential of becoming the scene of a bank robbery or burglary, or even a murder in the case that a bank robbery turns violent. Any number of air-sampling zones (labeled Zone 1, Zone 2, etc.) may be selected at the site. A zone of interest may be any location where a human (or animal) might cause an event that will be forensically investigated. Exemplary zones of interest include the entryways of a building, near expensive items subject to theft, furniture where people may sit, and so forth. A zone may be strategically selected to be in very close proximity to the orifices (nose, mouth, etc.) of a person, where increased concentrations of material may be expelled by the person. Examples of such positioning may be at about head-level of the average adult male, near fixtures (e.g. a sink or urinal) where a person might remain stationary for several moments while expelling material including fluids and gases (e.g. through breathing), near and around doorways where people enter and exit the site, and so forth.

A number of containers 20 are positioned at the site for collecting air samples. An airflow manifold 52 includes a network of airflow conduit 53 (e.g. plastic or metal tubing) connecting the containers 20 to a pump 54. In this embodiment, three containers 20A, 20B, and 20C are associated with Zone 1. This discussion will focus primarily on how air is sampled in Zone 1, by way of example. The pump 54 moves air from the zone of interest through one or more of the containers 20A-C via the airflow manifold 52. Inlet valves 24 and outlet valves 28 control airflow through each of the containers 20A-C. A controller 60 electronically connected to each set of the valves 24, 28 controls and automates the operation of the valves 24, 28 to flow air through one or more of the containers 20A-C and selectively capture air samples within the containers 20A-C. For example, a timer 62 included with the controller 60 may, at selected intervals, open the valves 24, 28 of selected containers to allow air to flow through the containers, then close the valves 24, 28 to capture the sampled air in the containers. Other pressure mechanisms or valve-operation techniques may be provided or performed to pressurize the captured samples within the containers, even to the point of liquefying the gases if desired, to increase the amount of material captured within each container.

Each container 20A-C used to collect an air sample from Zone 1 could be allocated for a different purpose or type of sample. In this example, the first container 20A may be used to capture and contain a control air sample, the second container 20B may be used to contain a "backup sample" (e.g. a redundant control sample), and the third container 20C may be used to contain the evidence sample. Thus, air samples may be periodically captured in the containers 20A and 20B prior to the occurrence of a potential event to be forensically investigated, and later used as control air samples if such an event does occur. The controller 60 may be programmed to periodically sample the air within each zone. For example, the valves 24, 28 to the containers 20A and 20B may be opened periodically to purge the contents of the containers 20A and 20B and to capture a new control air sample. To help ensure the control air sample is representative of the conditions at the time the control air sample is taken, the valves 24, 28 may be opened fully and air may be forcefully passed through the containers 20A, 20B to more fully remove the prior contents. This control air sampling may occur at regular intervals, such as once per hour, but need not necessarily occur with a regular frequency. The timer 62 may be used to determine when the samples are taken, according to programming of the controller 60. Additionally, the timer 62 may be used to mark the time at which each sample is taken, and those times may be recorded by the controller 60 so that the contents of the control air samples and evidence air samples may be associated with the time at which those samples were taken. Rather than purging the contents of each container 20 periodically, a succession of samples may instead be obtained using a different container each time. For example, a different container may be used each hour to contain a sample taken during that hour, so that each control air sample could be analyzed to show a progression (or lack thereof) of air content in the zone of interest during the hours preceding the event.

When a triggering event occurs in Zone 1, a sensor or alarm condition may signal the controller 60 to cause an evidence air sample to be captured within the container 20C. For example, a sensor may sense human activity within Zone 1 and send a signal to the controller 60 to capture the evidence air sample in the container 20C. The captured sample in the container 20C is preferably taken contemporaneously or close-in-time to the event. Subsequently, the evidence air sample contained within the container 20C may be analyzed to identify whether a human was present in Zone 1 and, if so, to identify the human. The evidence air sample may also be compared with the control sample in container 20A and the backup sample (if necessary) in container 20B to make such determinations. However, it is recognized that some events that will be forensically investigated are not detectable or predictable, such as in the case of an assault or murder. Thus, a sensor or alarm condition may not always be available to trigger the sampling of an evidence air sample in response to an event. Rather, the air samples that have been periodically taken may be stored so that if the event occurs, the air samples taken before, during, and after the event may be analyzed.

An odor detector (also known in the art as a "smell sensor") may also be included to supplement the forensic analysis. In the system of FIG. 3, for example, an odor detector 70 is included in Zone 2, for electronic detection of odors, or for airborne substances generally. Odors may be detected on a real-time or approximately real-time scale using the odor detector 70. A variety of odor detectors are known in the art.

One embodiment of the odor detector 70 includes a quartz crystal with electrical connections to the controller 60 and a special plastic coating. The plastic coating on the quartz crystal adsorbs some of the airborne gases and particles of the type that a human can smell. These particles may induce a vibration change in the quartz crystal to artificially sense odors. Because the vibration characteristics of a quartz crystal depend on its size, shape, stiffness, and mass, the change in vibration characteristics due to the adsorption of the airborne particles may be interpreted by the controller 60 to identify a particular substance or smell. Thus, the odor detector 70 may communicate signals to the controller 60 in real-time and, upon the occurrence of an event, the smells or airborne substances in Zone 2 may be identified and recorded by the controller 60. This data may be used in the subsequent forensic analysis, either alone or in combination with the analysis of the evidence air samples and control air samples.

FIG. 3 is schematic diagram of an exemplary site 100 equipped with the air sampling system 50. By way of example, the site 100 in this embodiment is a museum 100 with a priceless diamond 102 displayed on a pedestal 104 near the center of the museum 100. Due to the sheer value and appeal of the diamond 102, the museum 100 has the potential to attract thieves who desire to steal the diamond 102. Thus, in addition to numerous conventional safeguards, including an extensive intrusion alarm, a fortified building, and a video surveillance system 114, the museum 100 is equipped with a particular configuration of the air sampling system 50 (FIG. 3). Some of the details of the air sampling system 50 already shown and discussed in FIG. 2, such as the airflow manifold 52, are omitted here. The air sampling system 50 in this embodiment includes five zones (Zones 1-5). Zones 1 and 4 are positioned at entryways 106, 108. Zones 2 and 5 are positioned in an adjoining room 110, and Zone 5 is in close proximity to the diamond 102. Each of these zones includes an inlet port to a set of containers 20, which may be connected within the air sampling system 50 for sampling the air from the respective zones. The containers 20 may be used to sample the air in each of the five zones periodically, to obtain control air samples, and in response to an alarm condition, to obtain evidence air samples.

Numerous alarm conditions may trigger the collection of evidence air samples in the museum 100. For example, if the entryways 106, 108 are locked after-hours, the breaking and entering through either entryway 106, 108 may cause an alarm which triggers the sampling of air within Zones 1 and 4, respectively. For example, a proximity sensor 105 positioned at Zone 1 may detect entry through the entryway 106 after hours and generate an alarm signal to the controller 60, to trigger the sampling of air. The sampling of the air may be timed to occur a brief moment, such as within several seconds, after a thief has passed through the entryway 106, 108, to take a sample of air near in time and location to where and when the thief entered the museum 100. Another alarm system may be caused by the breaking of a lock 112 to gain access to the diamond 102. The containers 20 located in Zone 3 are hidden and secured within the pedestal 104, so that a thief is unlikely to take or sabotage the containers 20.

Figure 4:
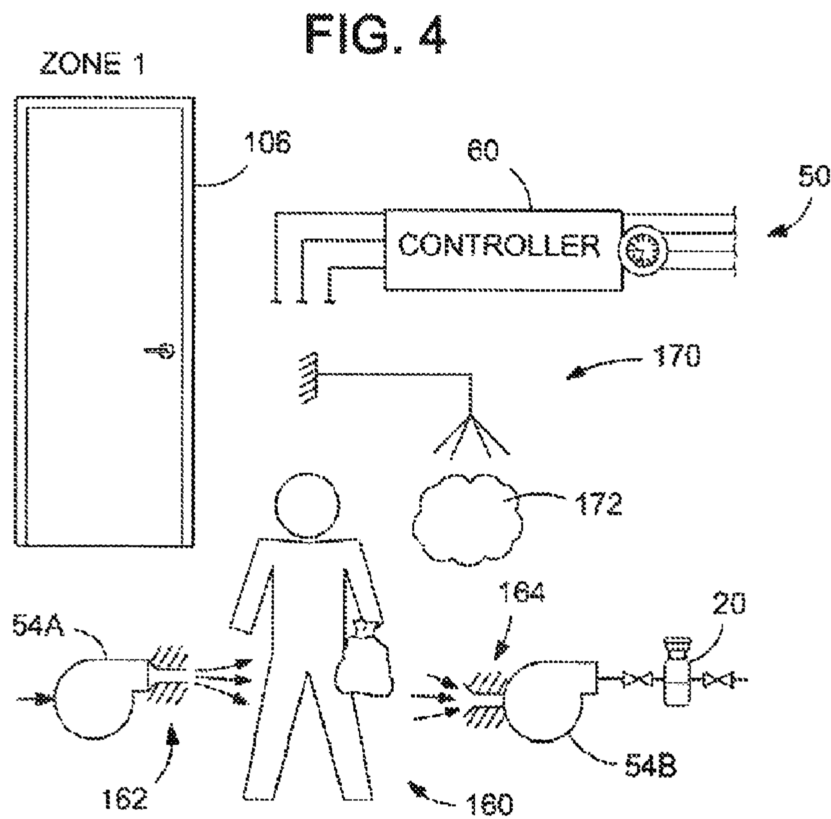
FIG. 4 is a schematic illustration of an induced expulsion system, for inducing the expulsion of material from the mammal.

FIG. 4 is a schematic illustration of an induced expulsion system 150, for inducing the expulsion of material from the person 10. In this embodiment, the induced expulsion system 150 is integrated with a portion of the air sampling system 50 (FIG. 3), and is positioned near the entryway 106. The induced expulsion system 150 causes or at least increases the likelihood that a sufficient quantity and type of organic material is obtained from the person 10 to produce a sample useful for forensic analysis (e.g. organic material containing DNA for use in a DNA identity determination). This embodiment of the induced expulsion system 150 includes both an increased-velocity airflow capture subsystem 160 and a sneeze induction subsystem 170. The airflow capture subsystem 160 includes an air nozzle 162 for directing a forceful stream of air (e.g. greater than 10 mph) at the person 10 near the entryway 106 at Zone 1, sufficient to dislodge surface material (e.g. hair and tissue) from the person 10. The air nozzle 162 is powered by a pump 54A. A cooperating vacuum intake nozzle 164 forcefully draws in air in the vicinity of the entryway 106 to intake air containing the dislodged surface material for capturing in the containers 20. A vacuum pump 54B powers the vacuum intake nozzle 164. The sneeze induction system 170 delivers a blast of a nasal irritant 172, such as pepper, talcum powder, or other substance, to induce the person 10 to sneeze as the person 10 enters the entryway 106. The timing and placement of the sneeze induction system 170 and nozzles 162, 164 are selected so that the person 10 will sneeze when in proximity to the induced expulsion system 160. Causing the person 10 to sneeze will increase the amount of material available for sampling and analysis. However, even without the sneeze induction system 170, the increased-velocity airflow capture subsystem helps increase the viability of the air samples for forensic analysis.

One skilled in the art might consider whether, instead of introducing a benign nasal irritant 172, to instead introduce a more lethal or debilitating substance, such as pepper spray, nerve gas, or a sleeping agent, into one of the zones. However, although such a substance might be effective at capturing or incapacitating a thief or other perpetrator, such practices are usually against public policy, and are oftentimes simply illegal. Numerous statutory and caselaw precedent has severely limited the legality and increased potential civil liability associated with the use of such extreme measures. Therefore, the airflow capture subsystem 160 and the sneeze induction subsystem 170 provide an alternative that will typically not induce bodily injury, but which may still be used to effectively identify perpetrators of a crime.

FIG. 5 is a flowchart outlining an embodiment of an air sampling method according to the invention. In step 200, an evidence acquisition system for selectively acquiring control air samples and evidence air samples is initiated. In step 202, ambient air in an airflow capture zone is flowed through a control container, such as a container, that will be used to selectively capture a control air sample prior to the occurrence of an event to be forensically investigated. In step 204, ambient air is flowed through an evidence container, such as another container, that will be used to selectively capture an evidence air sample after the occurrence of the event to be forensically investigated. According to step 206, zones of interest may be continuously monitored for an event. An event may be, for instance, the entrance of a mammal into the zone of interest, in which case examples of what may trigger the detection of the event include the opening of a door to the zone of interest, motion of the mammal within the zone of interest, or the breaking of an object (such as a container containing a valuable item) within the zone of interest. If the opening of a door triggers the event, but the event includes the presence of the mammal in the zone of interest, then the zone of interest may be expanded to include not only a room the mammal enters but also the door to the room that the mammal opens.

If an event is detected in step 208, then an evidence air sample is automatically captured in the evidence container in step 212. Step 210 optionally induces the release of biometric material from a person within the zone of interest prior to capturing the evidence air sample. For example, a sneezing agent may be introduced in step 210, or a forceful blast of air may be used to dislodge material from the person. In step 214, the evidence air samples are gathered. In step 216, the evidence air samples may be forensically analyzed. In step 218, the forensic analysis may be furthered by comparing the evidence air samples with each other and/or to the control air samples. If, in conditional step 208, no event is detected, then conditional step 220 is used to determine whether a selected interval has elapsed after which a new sample is automatically captured in step 222. If an event occurs that is not detectable in step 208, then the air samples captured in step 222 may still be used in the forensic analysis. An evidence air sample may be identified in that case according to the time each air sample was taken.

The terms "comprising," "including," and "having," as used in the claims and specification herein, shall be considered as indicating an open group that may include other elements not specified. The terms "a," "an," and the singular forms of words shall be taken to include the plural form of the same words, such that the terms mean that one or more of something is provided. The term "one" or "single" may be used to indicate that one and only one of something is intended. Similarly, other specific integer values, such as "two," may be used when a specific number of things is intended. The terms "preferably," "preferred," "prefer," "optionally," "may," and similar terms are used to indicate that an item, condition or step being referred to is an optional (not required) feature of the invention.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

What is claimed is:

1. A method, comprising:

automatically capturing, in a first sealed container, a control air sample from a zone of interest prior to an entrance of a mammal into the zone of interest;

automatically inducing the mammal to expel material and automatically capturing, in a second sealed container, an evidence air sample containing the expelled material after the entrance of the mammal into the zone of interest; and analyzing the material in the evidence air sample to identify characteristics of the mammal.

2. The method of claim 1, further comprising:

electronically detecting an event in the zone of interest caused by the mammal; and automatically capturing the evidence air sample in response to the electronic detection of the event.

3. The method of claim 1, wherein the characteristics of the mammal include the presence or identity of the mammal.

4. The method of claim 1, wherein analyzing the material in the evidence air sample includes performing a DNA analysis on the material.

5. The method of claim 1, wherein analyzing the material in the evidence air sample includes determining the concentration of gases in the evidence air sample.

6. The method of claim 1, wherein the material comprises DNA, methane, carbon dioxide, saliva, mucus, hair, skin, or a combination thereof.

7. The method of claim 1, wherein inducing the mammal to expel the material comprises introducing a sneezing agent into the zone of interest, and capturing the evidence air sample after the mammal has sneezed.

8. A method, comprising:

automatically capturing, in a first sealed container, a control air sample from a zone of interest prior to an entrance of a mammal into the zone of interest;

automatically directing an air stream at the mammal sufficient to remove surface material from the mammal;

automatically capturing, in a second sealed container, an evidence air sample containing the removed surface material after the entrance of the mammal into the zone of interest; and analyzing the material in the evidence air sample to identify characteristics of the mammal.

9. The method of claim 8, wherein the surface material includes skin cells or hair of the mammal.

10. A method, comprising:

automatically capturing, in a first sealed container, a control air sample from a zone of interest prior to an entrance of a mammal into the zone of interest;

automatically capturing, in a second sealed container, an evidence air sample containing material from the mammal after the entrance of the mammal into the zone of interest;

electronically detecting an odor present in one or both of the zone of interest and the evidence air sample; and analyzing the material in the evidence air sample to identify characteristics of the mammal.

11. A system, comprising:

an air-sampling container;

an airflow system configured for moving air from a zone of interest into the air-sampling container and selectively closing airflow to the air-sampling container;

a sneeze induction system configured to release a sneezing agent in the zone of interest in response to detection of an event caused by a mammal that enters the zone of interest; and a controller configured for selectively closing the airflow to the container in response to the event caused by the mammal that enters the zone of interest to capture an air sample from the zone of interest within the air-sampling container.

12. The system of claim 11, further comprising:

a sensor configured for detecting the event caused by the mammal and generating a signal to the controller in response thereto for selectively closing the airflow.

13. The system of claim 11, wherein the controller is configured to periodically release the captured air sample and capture another air sample within the air-sampling container.

14. A system, comprising:

an air-sampling container;

an airflow system configured for moving air from a zone of interest into the air-sampling container and selectively closing airflow to the air-sampling container;

a controller configured for selectively closing the airflow to the container in response to an event caused by a mammal that enters the zone of interest to capture an air sample from the zone of interest within the air-sampling container; and an odor detector in electronic communication with the controller, wherein the odor detector is configured to generate a signal representative of an airborne substance in the zone of interest.

15. A system, comprising:

an air-sampling container;

an airflow system configured for moving air from the zone of interest into the air-sampling container and selectively closing airflow to the air-sampling container;

an increased-velocity airflow capture subsystem configured for directing an airflow stream of at least 10 mph at a mammal within the zone of interest, to dislodge material from the mammal; and a controller configured for selectively closing the airflow to the container in response to an event caused by the mammal in the zone of interest to capture an air sample from the zone of interest within the air-sampling container.

16. The method of claim 1, further comprising:

comparing the evidence air sample to the control air sample to identify characteristics of the mammal or to verify the mammal was present in the zone of interest.

17. The method of claim 8, further comprising:

comparing the evidence air sample to the control air sample to identify characteristics of the mammal or to verify the mammal was present in the zone of interest.

18. The method of claim 10, further comprising:

comparing the evidence air sample to the control air sample to identify characteristics of the mammal or to verify the mammal was present in the zone of interest.

* * * * *